US006365750B1

(12) United States Patent
Thottathil et al.

(10) Patent No.: US 6,365,750 B1
(45) Date of Patent: Apr. 2, 2002

(54) METHODS FOR THE PREPARATION OF TAXANES USING OXAZOLIDINE INTERMEDIATES

(75) Inventors: John K. Thottathil, Robbinsville; Ivan D. Trifunovich, Belle Mead, both of NJ (US)

(73) Assignee: Bristol Myers Squibb Comp., Princeton, NJ (US)

( * ) Notice: Subject to any disclaimer, the term of this patent is extended or adjusted under 35 U.S.C. 154(b) by 0 days.

(21) Appl. No.: 09/315,712

(22) Filed: May 20, 1999

Related U.S. Application Data

(63) Continuation of application No. 08/845,299, filed on Apr. 25, 1997, now abandoned, which is a continuation of application No. 08/408,676, filed on Mar. 22, 1995, now abandoned.

(51) Int. Cl.[7] .............................................. C07D 263/06
(52) U.S. Cl. ........................ 548/215; 549/510; 549/511
(58) Field of Search ............................................ 548/215

(56) References Cited

U.S. PATENT DOCUMENTS

| 4,203,900 A | 5/1980 | Kaiser ........................ 269/999 |
| 4,303,439 A | 12/1981 | Howe et al. ................... 71/88 |
| 4,354,029 A | 10/1982 | Kaiser et al. ............... 548/239 |
| 4,360,678 A | 11/1982 | Howe et al. ................ 548/236 |
| 4,443,611 A | 4/1984 | Kaiser ........................ 548/239 |
| 4,543,414 A | 9/1985 | Larson ....................... 548/239 |
| 4,743,700 A | 5/1988 | Jommi et al. .............. 548/216 |
| 4,814,470 A | 3/1989 | Colin et al. ................. 514/449 |
| 4,857,653 A | 8/1989 | Colin et al. ................. 549/511 |
| 4,876,399 A | 10/1989 | Holton et al. .............. 508/817 |
| 4,877,881 A | 10/1989 | Belliotti et al. ............ 548/240 |
| 4,924,002 A | 5/1990 | Kostlan ...................... 548/206 |
| 4,924,011 A | 5/1990 | Denis et al. ................ 549/510 |
| 4,924,012 A | 5/1990 | Colin et al. ................. 549/510 |
| 4,942,184 A | 7/1990 | Haugwitz et al. ........... 514/449 |
| 4,960,790 A | 10/1990 | Stella et al. ................ 514/449 |
| 5,015,744 A | 5/1991 | Holton ........................ 549/510 |
| 5,059,669 A | 10/1991 | Kingston et al. ........... 549/511 |
| 5,128,478 A | 7/1992 | Ito et al. ..................... 548/237 |
| 5,136,060 A | 8/1992 | Holton ........................ 549/510 |
| 5,319,112 A | 6/1994 | Kingston et al. ........... 549/510 |
| 5,420,337 A | 5/1995 | Patel et al. .................... 560/41 |
| 5,576,450 A | 11/1996 | Bouchard et al. .......... 549/510 |
| 5,587,493 A | 12/1996 | Bouchard et al. .......... 549/510 |
| 5,606,083 A | * 2/1997 | Bouchard et al. .......... 549/510 |
| 5,616,739 A | * 4/1997 | Mas et al. ................... 549/510 |
| 5,637,723 A | * 6/1997 | Commercon et al. ....... 548/215 |

FOREIGN PATENT DOCUMENTS

| CA | 1061330 | 8/1979 |
| DE | 1695918 | 5/1971 |
| DE | 2701-751 | 7/1977 |
| DE | 2919891 | 12/1980 |
| EP | 027020 | 4/1981 |
| EP | 245825 | 11/1987 |
| EP | 336840 | 10/1989 |
| EP | 0359516 | 3/1990 |
| EP | 0400971 | 12/1990 |
| EP | 0428376 | 5/1991 |
| FR | 2698871 | 6/1994 |
| FR | 2706457 | 12/1994 |
| JP | 49135-968 | 12/1974 |
| JP | 77010-873 | 3/1977 |
| JP | 55-145650 | 11/1980 |
| JP | 60-222-416 | 11/1985 |
| JP | 61-005-015 | 1/1986 |
| JP | 61-115-022 | 6/1986 |
| JP | 61-51578 | 11/1986 |
| WO | 90/02738 | 3/1990 |
| WO | 92/09589 | 6/1992 |
| WO | WO/94/07877 | * 4/1994 |
| WO | 94/07877 | 4/1994 |
| WO | 94/07878 | 4/1994 |
| WO | WO94/07878 | * 4/1994 |
| WO | 94/10169 | 5/1994 |
| WO | 94/13654 | 6/1994 |
| WO | 94/29284 | 12/1994 |
| WO | 94/29288 | 12/1994 |
| WO | 95/20582 | 8/1995 |
| ZA | 91/9224 | 11/1991 |
| ZA | 93/7319 | 6/1994 |

OTHER PUBLICATIONS

Commercon et al., "Improved Protection and Esterification of a Precursor of the Taxotere® and Taxol Side Chains", Tetrahedron Letters, vol. 33, No. 36, pp. 5185–5188 (1992).

Boyd et al.; "Cyclization of Acylaminoalkanols to 2–Oxazolines"; JACS, vol. 82, pp. 2032–2034 (1960).

Boyd et al.; "Sulfonic Acid Esters as Alkylating Agents: Formation of 2–Oxazolines"; JACS, vol. 75, pp. 5896–5897 (1953).

Bubel et al.; "Reaction of Acetyloxiranes with Acetonitrile", Chem. Heterocycl. Compd. (Engl. Transl.), 18,8, pp. 773–775 (1982).

Cason et al.; "Syntheses in the Peri–Substituted Naphthalene Series", J. Org. Chem., vol. 15, pp. 617–626 (1950).

Corey et al., "Highly Enantioselective Routes to Darzens and Acetate Aldol Products from Achiral Aldehydes and t–Butyl Bromoacetate", Tetrahedron Letters, vol. 32, No. 25, pp. 2857–2860 (1991).

(List continued on next page.)

Primary Examiner—Ba K. Trinh
(74) Attorney, Agent, or Firm—Gabriel Lopez

(57) ABSTRACT

Novel oxazolidines finding utility as intermediates in the preparation of C-13 acyloxy sidechain-bearing taxanes such as paclitaxel and analogs thereof. The present invention also relates to novel methods of coupling the oxazolidines to form the aforementioned taxanes, and to methods of preparing the oxazolidines.

4 Claims, No Drawings

OTHER PUBLICATIONS

Deng et al., "A Practical, Highly Enantioselective Synthesis of the Taxol Side Chain via Asymmetric Catalysis", J. Org. Chem., vol. 57, pp. 4320–4323 (1992).

Denis et al., "Direct, Highly Efficient Synthesis from (S)–(+)– Phenylglycine of the Taxol and Taxotere Side Chains", J. Org. Chem., vol. 56, pp. 6939–6942 (1991).

Denis et al., "A Highly Efficient, Practial Approach to Natural Taxol", J. Am. Chem. Soc., vol. 110, pp. 5917–5919 (1988).

Denis et al., "An Improved Synthesis of the Taxol Side Chain and of RP 56976", J. Org. Chem., vol. 55, pp. 1957–1959 (1990).

Denis et al., "An Efficient, Enantioselective Synthesis of the Taxol Side Chain", J. Org. Chem., vol. 51, pp. 46–50 (1986).

Elliot, D.F., "The Stereochemistry of an Oxazoline Derivative of Threonine. Improvement of a Recent Threonine Synthesis", *J. Chem. Soc.* pp. 589–594 (1949).

Eliel et al, "Atrolactic Acid", col. vol. IV, Organic Syntheses, pp. 58–62 (1963).

Georg et al., "Asymmetric Synthesis of β–lactams and N–Benzoyl–3–Phenylisoserines Via the Staudinger Reaction", Tetrahedron Letters, vol. 32, No. 27, pp. 3151–3154 (1991).

Drefahl et al., Stereochemischer Verlauf von Ringschlubreaktionen der diastereomeren DL–1–Amino–1.2–diphenyl–propanole–(2), Chemische Berichte, 91, pp. 1092–1099 (1958).

Ghera et al., "Formation of $\Delta^2$–Oxazolines by Cyclization of N–Acyl–β–Hydroxy–amines on Zinc Acetate. An Oxazoline Complex of Zinc Acetate", J.C.S. Chem. Comm., pp. 639–640 (1972).

Harada et al., "Optical Resolution and Configuration of cis–β–Phenylglycidic Acid", Bulletin of the Chemical Society of Japan, vol. 47 (11), pp 2911–2912 (1974).

Hauptmann et al., The Synthesis of Cystine–β,β'–dicarboxylic Acid, J. Am. Chem. Soc., vol. 77, pp. 704–707 (1955).

Hauptmann et al., "Reaction of Trans–Epoxy–Succinic Acid with Ammonia and Amines: β–Hydroxyaspartic acid and its N–alkyl Derivatives", Anais Assoc. Brasil. Quin., 19, pp. 173–183 (1960) (also, Chemical Abstracts, vol. 57, 16732h).

Heine et al., "Aziridines. XVI. Isomerization of Some 1–Aroylaziridines", J. Org. Chem., 32, pp. 3069–3074 (1967).

Honig et al., "Chemo–Enzymatic Synthesis of All Isomeric 3–Phenylserines and Isoserines", Tetrahedron, vol. 46, No. 11, pp. 3841–3850 (1990).

Kato et al., "Studies on Ketene and Its Derivatives. XLII. Ring–Expansion of 1–Acetoacetylaziridine", vol. 91, pp. 384–392 (1971).

Kimball et al., "Ethyl α–Phenylacetoacetate", Organic Syntheses, Coll. vol. 2, pp. 284–286 (1943).

Magri et al., "Modified Taxols, 4. Synthesis and Biological Activity of Taxols Modified in the Side Chain", J. of Nat. Products, vol. 51, No. 2, pp. 298–306 (1988).

Nathansohn et al., "Steroids Possessing Nitrogen Atoms. IV Further Studies on the Synthesis of [17α, 16α,–d]–oxazolinocorticoids", *Steroids,* 13, pp. 383–397 (1969).

Ojima et al., "New and Efficient Routes to Norstatine and its Analogs with High Enantiomeric Purity by β–lactam Synthon Method", Tetrahedron Letters, vol. 33, No. 39, pp 5737–5740 (1992).

Ojima et al., "Efficient and Practical Asymmetric Synthesis of the Taxol C–13 Side Chain, N–Benzoyl–(2R, 3S)–3–phenylisoserine and Its Analogues via Chiral 3–Hydroxy–4–aryl–β–lactams through Chiral Ester Enolate–Imine Cyclocondensation", J. Org. Chem., 56, pp. 1681–1683 (1991).

Ojima et al., "New and Efficient Approaches to the Semisynthesis of Taxol and its C–13 Side Chain Analogs by Means of β–lactam Synthon Method", Tetrahedron, vol. 48, No. 34, pp. 6985–7012 (1992).

Pelchowicz et al., "Substituted Tryptamines and Their Derivatives", Journal of the Chemical Society, pp. 4699–4701 (1960).

Pfister et al., "The Synthesis of DL–Threonine. II. Interconversion of DL–Threonine and DL–Allothreonine", *JACS,* pp. 1101–1105 (1949).

Riordan et al., "Some Reactions of DL–trans–4, 5–Dicarbomethoxy–2–phenyl–2–oxazoline", J. Org. Chem., vol. 40, No. 22, pp. 3219–3221 (1975).

Schmidt et al., "Synthesis of (4R)–4–((E)–2–Butenyl)–4, N–Dimethyl–L–Threonine (MeBMT), The Characteristic Amino Acid of Cyclosporine", Tetrahedron Letters, vol. 28, No. 25, pp 2849–2852 (1987).

Solladie–Cavallo et al., "Synthesis of (2S, 3R)–3–Amino–2–hydroxy–5–methylhexanoic Acid: Bridging Effect of KF", J. Org. Chem., vol. 55, pp 4750–4754 (1990).

Wani et al., "Plant Antitumor Agents. VI. The Isolation and Structure of Taxol, a Novel Antileukemic and Antitumor Agent from *Taxus brevifolia*"; J. Amer. Chem. Society, pp. 2325–2327 (1971).

Zvonkova et al., "Synthesis of a Structural Analog of Sphingomyelin", J. Org. Chem. USSR (Engl. Transl.), 10, pp. 1637–1640 (1974).

Gou et al., "A Practical Chemoenzymatic Synthesis of the Taxol C–13 Side Chain N–Benzoyl–(2R, 3S)–3–phenylisoserine", J. Org. Chem., 58, pp. 1287–1289 (1993).

Magri, "Modified Taxols as Anticancer Agents", Dissertation submitted to the Faculty of the Virginia Polytechnic Institute and State University, pp. 55–68 (Aug., 1985).

Kingston et al., "Synthesis of Taxol from Baccatin III via an Oxazoline Intermediate", Tetrahedron Letters, 35(26), 4483–4484 (1994).

M. Pasto et al., Chemical Abstracts, vol. 124, No. 5, Jan. 29, 1996, Columbus, Ohio, US; abstract No. 56628g (abstract); Tetrahedron: Asymmetry, vol. 6, No. 9, 1995, Oxford, GB, pp 2329–2342.

L. L. Klein et al., Chemical Abstracts, vol. 121, No. 25, Dec. 19, 1994, Columbus, Ohio, US; abstract No. 301093s (abstract); Tetrahedron Letters, vol. 35, No. 27, 1994, Oxford, GB, pp 4707–4710.

Denis et al., *Tetrahedron Letters,* 35(1), 105–8 (1994).

Dondoni et al., *Synthesis,* 181–6 (1995).

Commercon et al, Tetrahedron Letters, 33(36), pp. 5185–5188, 1992.*

* cited by examiner

METHODS FOR THE PREPARATION OF TAXANES USING OXAZOLIDINE INTERMEDIATES

This is a continuation of Ser. No. 08/845,299, Apr. 25, 1997, abandoned, which is a continuation of Ser. No. 08/408,676, Mar. 22, 1995, abandoned.

FIELD OF THE INVENTION

The present invention relates to novel oxazolidines which find utility as intermediates in the preparation of C-13 acyloxy sidechain-bearing taxanes such as paclitaxel and analogs thereof. The present invention also relates to novel methods of preparing the oxazolidines, as well as to novel methods of coupling the oxazolidines to form the aforementioned sidechain-bearing taxanes.

BACKGROUND OF THE INVENTION

Taxanes are diterpene compounds finding utility in the pharmaceutical field. For example, paclitaxel (Taxol®), a taxane having the structure:

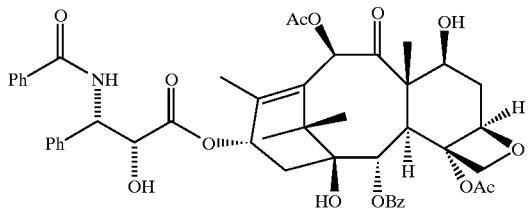

where Ph is phenyl, Ac is acetyl and Bz is benzoyl, has been found to be an effective anticancer agent. The compound taxotere, having the following structure, has also been reported for anticancer use:

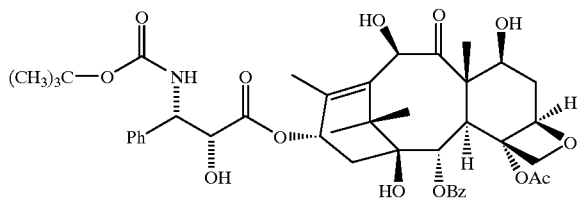

Naturally occurring taxanes such as paclitaxel may be found in plant materials, and have been isolated therefrom. Such taxanes may, however, be present in plant materials in relatively small amounts so that, in the case of paclitaxel, for example, large numbers of the slow-growing yew trees forming a source for the compound may be required. The art has thus continued to search for synthetic, including semi-synthetic routes for the preparation of naturally occurring taxanes such as paclitaxel, as well as routes for the preparation of pharmaceutically useful analogs thereof. In particular, efficient. methods for the addition of a C-13 acyloxy sidechain to a taxane core are sought as the presence of the C-13 acyloxy sidechain imparts pharmacological activity or provides a taxane more readily converted to one having such pharmacological activity.

SUMMARY OF THE INVENTION

The present invention provides novel oxazolidine compounds useful as intermediates for the preparation of C-13 acyloxy sidechain-bearing taxanes. Novel methods for coupling the oxazolidine intermediates of the invention with taxanes containing a hydroxyl group directly bonded at C-13 to provide the aforementioned C-13 acyloxy sidechain-bearing taxanes are also provided, as are methods of preparing the novel oxazolidines of the present invention.

In particular, novel oxazolidines of the formulae I and II are provided:

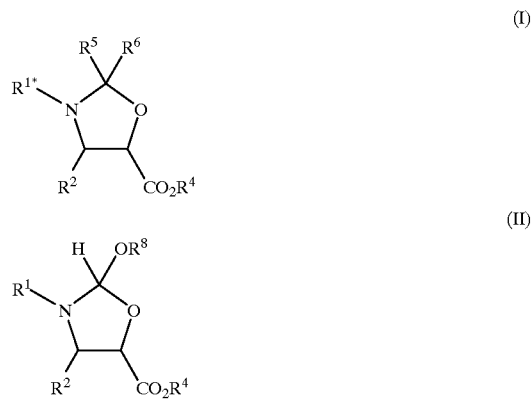

where $R^1$ is hydrogen, arylcarbonyl, alkoxycarbonyl or alkylcarbonyl;

$R^{1*}$ is hydrogen, arylcarbonyl, alkoxycarbonyl or alkylcarbonyl, with the proviso that $R^{1*}$ is not tert-butoxycarbonyl when $R^2$ is aryl;

$R^2$ is aryl, heterocyclo or alkyl;

$R^4$ is hydrogen, alkyl, alkenyl, alkynyl, aryl, cycloalkyl, cycloalkenyl, or heterocyclo;

$R^5$ and $R^6$ are (a) each independently alkyl; or (b) together with the carbon atom to which they are bonded, form a cycloalkyl, cycloalkenyl or heterocyclo group; and $R^8$ is alkyl or aryl;

and salts thereof.

The novel oxazolidines of the present invention are useful as intermediates in the preparation of C-13 acyloxy sidechain-bearing taxanes such as paclitaxel and analogs thereof. Thus, the present invention further provides novel methods for coupling the intermediates of the formulae I and II with a taxane containing a hydroxyl group directly bonded at C-13 to provide C-13 acyloxy sidechain-bearing taxanes of the following formula VI:

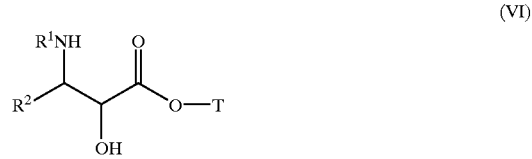

where $R^1$ is hydrogen, arylcarbonyl, alkoxycarbonyl or alkylcarbonyl; $R^2$ is aryl, heterocyclo or alkyl; and T is a taxane moiety directly bonded at C-13 of said moiety. Coupling may be achieved by the methods described following.

In one embodiment of the invention, a compound of the formula VI or salt thereof may be prepared by a method comprising the steps of:

(a) contacting a compound of the following formula III or salt thereof:

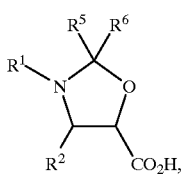
(III)

with a compound of the following formula IV:

HO—T    (IV), in the presence of a coupling agent, to form a compound of the following formula V or salt thereof:

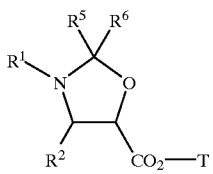
(V)

where $R^1$, $R^2$, $R^5$, $R^6$ and T are as defined above; and (b) contacting said compound of the formula V or salt thereof with a ring-opening agent to form said compound of the formula VI or salt thereof. Each of the steps (a) (when $R^1$ is $R^{1*}$) and (b) of this method are themselves novel methods. Additionally, the compounds of the formulae III and V and salts thereof are novel when $R^1$ is $R^{1*}$.

Compounds of the formula III include compounds of the formula I where $R^4$ is hydrogen. A compound of the formula I where $R^4$ is other than hydrogen may be converted to a compound of the formula III where $R^1$ is $R^{1*}$ by a novel method comprising the step of hydrolyzing said compound of the formula I where $R^4$ is other than hydrogen to form said compound of the formula III. Any compound capable of effecting the hydrolysis may be employed as the hydrolyzing agent. Exemplary hydrolyzing agents include aqueous bases such as aqueous hydroxides (e.g., metal hydroxides such as barium hydroxide, or preferably, alkali metal hydroxides such as lithium, sodium or potassium hydroxide). Contact with a base provides a carboxylic acid salt of a compound of the formula III. Further contact with an acid, preferably a mineral acid such as HCl, provides a compound of the formula III where $R^4$ is hydrogen, that is, which contains a free carboxylic acid group. Compounds of the formula III where $R^1$ is other than $R^{1*}$ may be prepared by methods analogous to those methods described herein for the preparation of compounds of the formula III where $R^1$ is $R^{1*}$.

In another embodiment of the invention, a compound of the formula VI or salt thereof may be prepared by a method comprising the steps of:

(a) contacting a compound of the following formula VII or salt thereof:

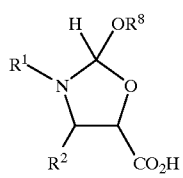
(VII)

with a compound of the following formula IV:

HO—T    (IV), in the presence of a coupling agent, to form a compound of the following formula VIII or salt thereof:

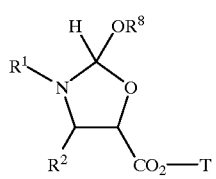
(VIII)

where $R^1$, $R^2$, $R^8$ and T are as defined above; and (b) contacting said compound of the formula VIII or salt thereof with a ring-opening agent to form said compound of the formula VI or salt thereof. Each of the steps (a) and (b) of this method are themselves novel methods. Additionally, the compounds of the formulae VII and VIII and salts thereof are novel.

Compounds of the formula VII are compounds of the formula II where $R^4$ is hydrogen. A compound of the formula II where $R^4$ is other than hydrogen may be converted to a compound of the formula VII by a novel method comprising the step of hydrolyzing said compound of the formula II where $R^4$ is other than hydrogen to form said compound of the formula VII. Hydrolysis of a compound of the formula II to form a compound of the formula VII may be conducted as described above for the hydrolysis of a compound of the formula I where $R^4$ is other than hydrogen to form a compound of the formula III.

The ring of the present oxazolidine compounds is numbered herein as follows:

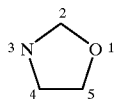

With respect to the 4- and 5-position carbon atoms, the oxazolidine compounds of the formulae I and II may exist as the four stereoisomers Ia or IIa, Ib or IIb, Ic or IIc and Id or IId, respectively, as follows:

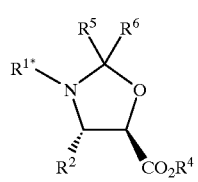
(Ia)

-continued

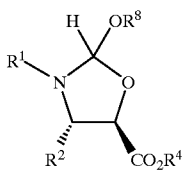
(IIa)

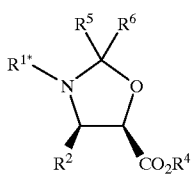
(Ib)

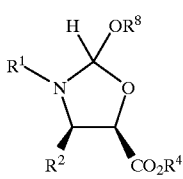
(IIb)

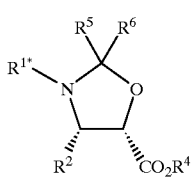
(Ic)

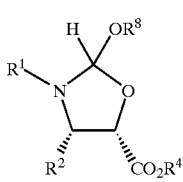
(IIc)

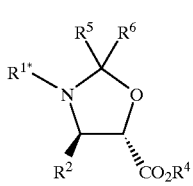
(Id)

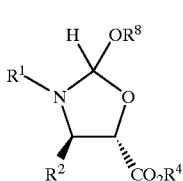
(IId)

As the stereochemistry of taxanes may affect their pharmaceutical activity, it is desirable to employ oxazolidine intermediates which will provide the final taxane product with the stereochemistry sought. While the use of stereoisomeric mixtures of a compound of the formula I or II is contemplated herein, the use of a single stereoisomer providing the desired stereochemistry in the final product may achieve a more efficient use of the starting materials and less complicated separation and purification procedures.

DETAILED DESCRIPTION OF THE INVENTION

The present invention is described further as follows.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl", as used herein, denote such optionally substituted groups as described above for alkyl having 1 to 6 carbon atoms in the normal chain.

The terms "alkoxy" or "alkylthio", as used herein, denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyl", as used herein, denotes an alkyl group bonded through a carbonyl group. The term "alkylcarbonyloxy", as used herein, denotes an alkylcarbonyl group which is bonded through an oxygen linkage. The terms "monoalkylamino" or "dialkylamino" denote an amino group substituted by one or two alkyl groups as described above, respectively.

The term "alkenyl", as used herein alone or as part of another group, denotes such optionally substituted groups as described for alkyl, further containing at least one carbon to carbon double bond. Exemplary substituents include one or more alkyl groups as described above, and/or one or more groups described above as alkyl substituents.

The term "alkynyl", as used herein alone or as part of another group, denotes such optionally substituted groups as described for alkyl, further containing at least one carbon to carbon triple bond. Exemplary substituents include one or more alkyl groups as described above, and/or one or more groups described above as alkyl substituents.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above, and/or groups described above as alkyl substituents.

The term "arylcarbonyl", as used herein alone or as part of another group, denotes an aryl group as described above bonded through a carbonyl group.

The terms "heterocyclo" or "heterocyclic", as used herein alone or as part of another group, denote optionally substituted, fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, benzofurazanyl, and especially, tetrahydropyranyl (e.g. 4-tetrahydropyranyl). Exemplary substituents include one or more alkyl groups as described above, and/or one or more groups described above as alkyl substituents.

The terms "halogen" or "halo", as used herein alone or as part of another group, denote chlorine, bromine, fluorine, and iodine.

The term "taxane moiety", as used herein, denotes moieties containing the core structure:

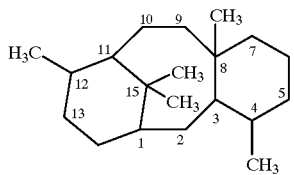

which core structure may be substituted and which may contain ethylenic unsaturation in the ring system thereof. Such moieties having an oxetane ring fused at the 4- and 5-positions, and an ethylenic double bond between C-11 and C-12, such as are found in paclitaxel, are preferred.

The term "taxane", as used herein, denotes compounds containing a taxane moiety as described above. The term "C-13 acyloxy sidechain-bearing taxane", as used herein, denotes compounds containing a taxane moiety as described above, further containing an acyloxy sidechain directly bonded to said moiety at C-13 through the oxygen of the oxy group of the acyloxy substituent.

The term "hydroxy (or hydroxyl) protecting group", as used herein, denotes any group capable of protecting a free hydroxyl group which, subsequent to the reaction for which it is employed, may be removed without destroying the remainder of the molecule. Such groups, and the synthesis thereof, may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, 1-methoxy-1-methylethyl, benzyloxymethyl, (β-trimethylsilylethoxy) methyl, tetrahydropyranyl, 2,2,2-trichloroethoxycarbonyl, t-butyl(diphenyl)silyl, trialkylsilyl, trichloromethoxycarbonyl, and 2,2,2-trichloroethoxymethyl.

The term "salt", as used herein, includes salts with organic and/or inorganic acids and/or bases.

The term "acyl", as used herein alone or as part of another group, denotes the moiety formed by removal of the hydroxyl group from the group —COOH of an organic carboxylic acid. The term "acyloxy", as used herein alone or as part of another group, denotes an acyl group as described above bonded through an oxygen linkage (—O—).

Preparation of oxazolidines of the Formulae I and II

The oxazolidines of the formulae I and II and salts thereof may be prepared starting with a compound of the following formula i:

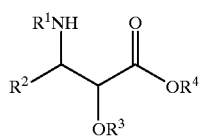

(i)

where $R^1$ is hydrogen, arylcarbonyl, alkoxycarbonyl or alkylcarbonyl; $R^2$ is aryl, heterocyclo or alkyl; $R^4$ is hydrogen, alkyl, alkenyl, alkynyl, aryl, cycloalkyl, cycloalkenyl or heterocyclo; and where $R^3$ is hydrogen or the group $R^{3P}$, where $R^{3P}$ is the group:

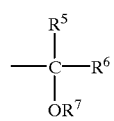

where $R^5$ and $R^6$ are as defined above, and $R^7$ is alkyl or aryl. Compounds of the formula i may be prepared as described in, or by methods analogous to those described in, U.S. application Ser. No. 07/975,453, filed Nov. 12, 1992, or U.S. application Ser. No. 08/263,869, filed Jun. 21, 1994, or as described below.

Compounds of the formula I and salts thereof may be prepared from compounds of the formula i and salts thereof where $R^1$ is $R^{1*}$ by a novel method comprising the step of contacting said compound of the formula i or salt thereof with an acid catalyst, and additionally, where $R^3$ in said compound of the formula i or salt thereof is hydrogen, with a compound of the formula ii or iii described following. The aforementioned compounds of the formulae ii and iii have the following structures:

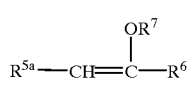

(ii)

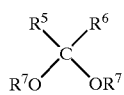

(iii)

where $R^5$, $R^6$ and $R^7$ are as defined above, and where $R^{5a}$ (i) is a group such that $R^{5a}$—$CH_2$— is $R^5$ or (ii) forms, together with $R^6$ and the atoms to which $R^{5a}$ and $R^6$ are bonded, a cycloalkenyl or heterocyclo group containing at least one carbon to carbon double bond. Compounds of the formulae ii and iii are commercially available or may readily be prepared by known methods. Exemplary compounds of the formula ii include the compounds:

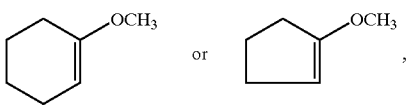

or, most preferably, 2-methoxypropene. Exemplary compounds of the formula iii include the compounds: dimethoxypropane,

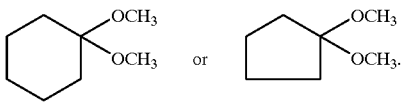

Novel compounds of the following formula iv and salts thereof:

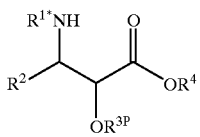

(iv)

where $R^{1*}$, $R^2$, $R^{3P}$ and $R^4$ are as defined above may be formed as intermediates in the aforementioned method when a compound of the formula i or salt thereof in which $R^3$ is hydrogen is contacted with the compound of the formula ii or iii. In the presence of acid catalyst, the compound iv or salt thereof undergoes conversion to a compound of the formula I or salt thereof.

Compounds of the formula II and salts thereof may be prepared from compounds of the formula i and salts thereof by a novel method comprising the step of contacting a compound of the formula i or salt thereof where $R^3$ is hydrogen, in the presence of an acid catalyst, with a compound of the following formula vi:

$HC(OR^8)_3$ (vi)

where $R^8$ is as defined above. Compounds of the formula vi are commercially available or may readily be prepared by known methods. Exemplary compounds of the formula vi include trimethoxymethane and triethoxymethane.

Novel compounds of the following formula v and salts thereof:

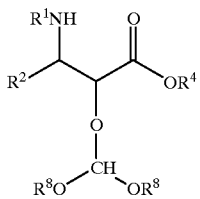

(v)

where $R^1$, $R^2$, $R^4$ and $R^8$ are as defined above may be formed as intermediates in the aforementioned method. In the presence of acid catalyst, the compound v or salt thereof undergoes conversion to a compound of the formula II or salt thereof.

For the conversion of a compound i to a compound I or II as described above, the present methods employ an "acid catalyst". Any acid catalyzing the method referred to may suitably be employed as the acid catalyst, with organic sulfonic acids (that is, organic acids containing the group $SO_2O^-$) or sulfonates, or mineral acids being preferred. Particularly preferred such acid catalysts include pyridinium p-toluene sulfonate (PPTS), toluene sulfonic acid, camphor sulfonic acid, and the like.

The compounds of the formula i and salts thereof may exist as four stereoisomers with respect to the carbon atoms at those positions corresponding to the 4- and 5-position carbon atoms of the compounds of the formulae I and II. These stereoisomers are the following compounds of the formulae ia, ib, ic and id:

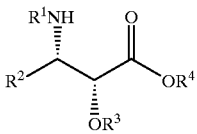

(ia)

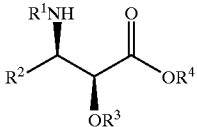

(ib)

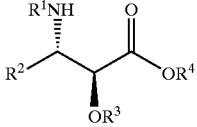

(ic)

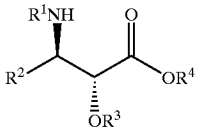

(id)

A desired stereoisomer of a compound of the formula I or II or salt thereof may be prepared by the methods described above by employing the appropriate stereoisomer of the starting compound of the formula i or salt thereof. Thus, use of a compound ia can provide a compound Ia or IIa, use of a compound ib can provide a compound Id or IId, use of a compound ic can provide a compound Ic or IIc, and use of a compound id can provide a compound Ib or IIb. It is preferred to employ a single stereoisomer of the starting compound i or salt thereof in the above described methods, although stereoisomeric mixtures may also be employed. Use of a compound ia to prepare a compound Ia or IIa is particularly preferred.

Coupling to Prepare Oxazolidine Sidechain-bearing Taxanes

An oxazolidine sidechain-bearing taxane of the formula V or VIII or salt thereof may be prepared by a method comprising the step of contacting an oxazolidine compound of the formula III or VII, respectively, or salt thereof, in the presence of a coupling agent, with a taxane of the formula IV having a hydroxyl group directly bonded to C-13 thereof. The taxane starting material of the formula IV is preferably a compound such as those described in European Patent Publication No. 400,971, incorporated herein by reference, or a compound such as those described in U.S. patent application Ser. No. 08/995,443, filed Dec. 23, 1992 by Poss et al., or continuation-in-part thereof U.S. patent application Ser. No. 08/171,792, filed Dec. 22, 1993, both also incorporated herein by reference. Exemplary such taxanes include those of the following formula IX:

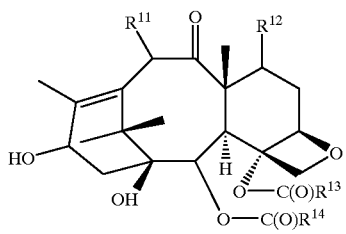

(IX)

where

R[11] is hydrogen, hydroxyl, $R^{15}$—O—, $R^{16}$—C(O)—O—, or $R^{16}$—O—C(O)—O—;

R[12] is hydrogen, hydroxyl, fluoro, $R^{15}$—O—, $R^{16}$—C(O)—O— or $R^{16}$—O—C(O)—O—;

R[13] and R[14] are independently hydrogen, alkyl, alkenyl, alkynyl, cycloalkyl, cycloalkenyl, aryl, or heterocyclo;

R[15] is a hydroxyl protecting group; and

R[16] is hydrogen, alkyl, alkenyl, alkynyl, cycloalkyl, cycloalkenyl, aryl or heterocyclo, or salts thereof.

All stereoconfigurations of the unspecified chiral centers of the compound of the formula IX are contemplated for use in the coupling method of the present invention. The use of a single stereoisomer is preferred, although mixtures thereof may be employed. 7-Trialkylsilyl baccatin III compounds are preferably employed as the compounds of the formula IV, most preferably, 7-trimethylsilyl baccatin III or 7-triethylsilyl baccatin III.

Any compound capable of effecting the coupling reaction may be employed as the coupling agent of the present invention. Exemplary coupling agents include one or more compounds forming an activated oxazolidine ester (for example, 1-hydroxybenzotriazole or N-hydroxysuccinimide, both of these with dicyclohexylcarbodiimide (DCC)) or anhydride (for example, an acid chloride such as pivaloyl chloride or bis(2-oxo-3-oxazolidinyl)-phosphinic chloride) when contacted with an oxazolidine of the formula III or VII, particularly coupling agents comprising a compound such as a carbodiimide (e.g., dicyclohexylcarbodiimide (DCC), 1,3-diisopropylcarbodiimide (DIC), or 1-(3-dimethylaminopropyl)-3-ethyl-carbodiimide hydrochloride), bis(2-oxo-3-oxazolidinyl)phosphinic chloride), carbonyl diimidazole (CDI), pivaloyl chloride, or 2,4,6-trichlorobenzoyl chloride; wherein the aforementioned compounds are preferably employed together with a compound such as 1-hydroxybenzotriazole (HOBt) or N-hydroxysuccinimide (HO-Su), or an amine such as triethylamine, pyridine or pyridine substituted at the 4-position with —N($R^{17}$)($R^{18}$), where $R^{17}$ and $R^{18}$ are independently selected from alkyl, alkenyl, alkynyl, cycloalkyl, cycloalkenyl or heterocyclo (to form a compound such as 4-dimethylaminopyridine (DMAP)), or where $R^{17}$ and $R^{18}$, together with the nitrogen atom to which they are bonded, form a heterocyclo group (to form a compound such as 4-morpholinopyridine or 4-pyrrolidinopyridine).

Ring Opening to Form Taxanes of the Formula VI

A sidechain-bearing taxane of the formula VI or salt thereof may be prepared from an oxazolidine sidechain-bearing taxane of the formula V or VIII or salt thereof, by a method comprising the step of contacting said taxane of the formula V or VIII or salt thereof with a ring-opening agent capable of opening the ring of the oxazolidine group bonded through C-13 of the taxane noiety. of said taxane compound to form said taxane compound of the formula VI or salt thereof.

A preferred class of ring-opening agents for the conversion of a compound V or salt thereof to a compound VI or salt thereof are Lewis acids which preferably cause minimal or, most preferably, no decomposition of the compounds V or VI or salts thereof ("mild Lewis acids"). Any Lewis acid capable of effecting the aforementioned ring opening may be employed in the method of the present invention. Exemplary such agents include palladium containing agents such as $Pd(CH_3CN)_2Cl_2$.

A preferred class of ring-opening agents for the conversion of a compound VIII or salt thereof to a compound VI or salt thereof are protic acids. Any protic acid capable of effecting the aforementioned ring opening may be employed in the method of the present invention. Exemplary such ring-opening acids include organic carboxylic acids, such as acetic acid or trifluoroacetic acid, and/or mineral acids such as hydrochloric acid, hydrofluoric acid or sulfuric acid, in water.

The compounds of the formula VI and salts thereof may exist as four stereoisomers with respect to the carbon atoms at those positions corresponding to the 4- and 5-position carbon atoms of the compounds of the formulae I and II. These stereoisomers are the following compounds of the formulae VIa, VIb, VIc and VId:

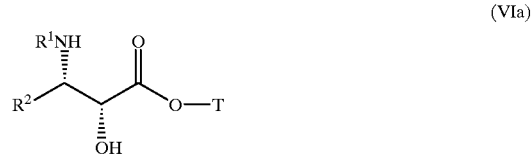

(VIa)

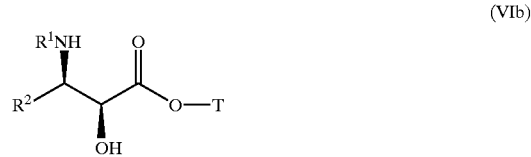

(VIb)

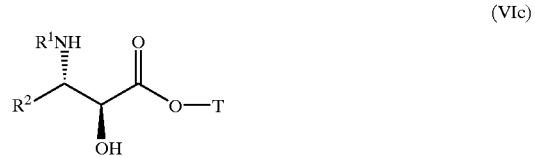

(VIc)

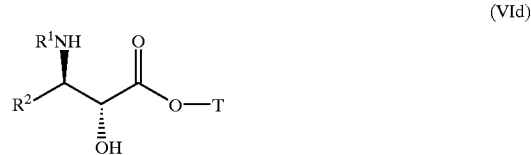

(VId)

A desired stereoisomer of the compound of the formula VI or salt thereof may be prepared by the methods described above by employing the appropriate stereoisomer of the starting compound of the formula III or VII or salt thereof. Using the designations "a" through "d" to refer to the stereoisomers of the formulae III and VII as are used for the compounds I and II above: use of a compound IIIa or VIIa will provide a compound VIa; use of a compound IIId or VIId will provide a compound VIb; use of a compound IIIc or VIIc will provide, predominantly, a compound VIa along with a minor amount of a compound VIc; and use of a compound IIIb or VIIb will provide, predominantly, a compound VIb along with a minor amount of a compound VId.

It is preferred to employ a single stereoisomer of the starting compound III or VII or salt thereof in the above described methods, although stereoisomeric mixtures may also be employed. Use of a compound Ia to prepare a compound VIa is particularly preferred.

A preferred embodiment of the present invention further comprises the step of deprotecting one or more groups, particularly to free hydroxyl groups, on the taxane moiety to prepare taxanes of the formula VI or salts thereof. Deprotection may, for example, be conducted prior or subsequent to, or simultaneously with, the aforementioned ring opening methods by use of a deprotection agent. Any compound capable of deprotection may be employed as the deprotection agent. For example, acids such as hydrofluoric acid or aqueous protic acids, or tetra-alkylammonium fluorides such am tetra-n-butylammonium fluoride, may be employed for removal of silyl protecting groups; benzyl protecting groups may be removed by hydrogenation; trichloroethoxycarbonyl protecting groups may be removed by contact with zinc; and acetal or ketal protecting groups may be removed by the use of protic acids or Lewis acids.

A particularly preferred embodiment of the present invention comprises simultaneous ring opening and deprotection of one or more hydroxyl groups on the taxane ring structure, particularly at C-7, such as by the use of an acid (e.g., a mineral acid such as hydrochloric acid) capable of effecting both ring opening and deprotection simultaneously. Thus, for example, use of an acid agent under reaction conditions described above for ring opening may allow simultaneous ring opening and deprotection of cleavable hydroxyl protecting groups at C-7 such as trialkylsilyl (e.g. trimethylsilyl or triethylsilyl).

Preferred Reaction Conditions

The methods of the present invention may be conducted under any conditions, such as temperature, pressure and time, and using the appropriate starting materials and catalysts in any relative amount, effective to achieve the desired conversion. Similarly, a solvent may be employed if desired and may be selected from any material in which the conversion may be conducted, including inorganic (e.g., aqueous) or organic (e.g., acetone, dimethylformamide, tetrahydrofuran, methylene chloride, acetonitrile, benzene or toluene) liquids or mixtures thereof. Solvents are preferably employed which are inert to the reaction.

The products of the methods of the present invention may be isolated and purified by any suitable methodology such as extraction, distillation, crystallization, column chromatography, and the like.

Particularly preferred reaction conditions for conducting various methods described herein are set forth in the following Tables 1 to 6.

Salts or solvates such as hydrates of reactants or products may be employed or prepared as appropriate in any of the methods of the present invention. Unless otherwise indicated, reference to a compound herein is understood to include salts and/or solvents thereof.

TABLE 1

Preferred Reaction Conditions for the Preparation of a Compound of the Formula I

| | |
|---|---|
| starting compounds | i; and ii or iii when $R^3$ = H in i |
| molar ratio of ii or iii:i | molar excess of ii or iii:i |
| catalyst | acid catalyst |
| molar ratio of | 0.03:1 to 0.1:1 |

TABLE 1-continued

Preferred Reaction Conditions for the Preparation of a Compound of the Formula I

| | |
|---|---|
| catalyst: i | |
| temperature (° C.) | 80 to 110 |
| Pressure (atm) | atmospheric |
| atmosphere | gas inert to reaction |
| solvent | organic |
| amount of solvent (weight of i: volume of solvent) | 1 g:50 ml to 1 g:100 ml |

Compound iv can be formed as an intermediate and converted to a compound of the formula I in situ due to the presence of acid catalyst, or contacted with acid catalyst in a separate step.

TABLE 2

Preferred Reaction Conditions for the Preparation of a Compound of the Formula II

| | |
|---|---|
| starting compound | i ($R^3$ = H) and vi |
| molar ratio of vi:i | molar excess of vi:i |
| catalyst | acid catalyst |
| molar ratio of catalyst: i | 0.03:1 to 0.1:1 |
| temperature (° C.) | 80 to 110 |
| pressure (atm) | atmospheric |
| atmosphere | gas inert to reaction |
| solvent | organic |
| amount of solvent (weight of i:volume of solvent) | 1 g:50 ml to 1 g:100 ml |

Compound v can be formed as an intermediate and converted to a compound of the formula II.

TABLE 3

Preferred Reduction Conditions for the Preparation of a Compound of the Formula III or VII

| | |
|---|---|
| starting compound | I or II (where $R^4$ ≠ H); and base |
| molar ratio of base:I or II | 1:1 to 1.05:1 |
| further starting material | acid |
| molar ratio of acid:I or II | 1:1 to 1.05:1 |
| temperature (° C.) | room (~25° C.) |
| pressure (atm) | atmospheric |
| atmosphere | gas inert to reaction |
| solvent | aqueous/organic mixture |
| amount of solvent (weight of I or II: volume of solvent) | 1 g:50 ml to 1 g:100 ml |

As described above, use of the base only can provide a formula III or VII salt; further use of an acid provides the free carboxylic acid.

TABLE 4

Preferred Reaction Conditions for the Preparation of a Compound of the Formula V or VIII

| | |
|---|---|
| starting compound | III or VII; and IV |
| molar ratio of III or VII:IV | molar excess of III or VII:IV, especially molar ratio of 1.1:1 to 1.5:1 |
| coupling agent | carbodiimide or |

TABLE 4-continued

Preferred Reaction Conditions for the Preparation
of a Compound of the Formula V or VIII

| | |
|---|---|
| molar ratio of carbodiimide or phosphinic chloride:III or VII | phosphinic chloride and amine 1.5:1 to 1:1 |
| molar ratio of amine:III or VII | 0.5:1 to 1:1 |
| temperature (° C.) | 60 to 100 |
| Pressure (atm) | atmospheric |
| atmosphere | gas inert to reaction |
| solvent | organic |
| amount of solvent (weight of III or VII: volume of solvent) | 1 g:5 ml to 1 g:10 ml |

TABLE 5

Preferred Reaction Conditions for the Preparation
of a Compound of the Formula VI Using Protic Acid

| | |
|---|---|
| starting compound | VIII; and protic acid (especially, aqueous protic acid) |
| molar ratio of acid:VIII | molar excess of acid: VIII |
| temperature (° C.) | 0 to 25 |
| pressure (atm) | atmospheric |
| atmosphere | gas inert to reaction |
| solvent | aqueous/organic |
| amount of solvent (weight of VIII: volume of solvent) | 1 g:10 ml to 1 g:20 ml |

TABLE 6

Preferred Reaction Conditions for the Preparation
of a Compound of the Formula VI Using Lewis acid

| | |
|---|---|
| starting compound | V; and Lewis acid (especially, mild Lewis acid) |
| molar ratio of Lewis acid:V | 0.02:1 to 0.1:1 |
| temperature (° C.) | room (~25° C.) |
| Pressure (atm) | atmospheric |
| atmosphere | gas inert to reaction |
| solvent | organic |
| amount of solvent (weight of V: volume of solvent) | 1 g:5 ml to 1 g:15 ml |

Preferred Groups

Preferred groups forming part of compounds used or prepared by the present invention are those where:

$R^1$ and $R^{1*}$ are each independently arylcarbonyl (especially benzoyl) or alkyloxycarbonyl (especially unsubstituted lower alkyloxycarbonyl such as tert-butoxycarbonyl);

$R^2$ is phenyl, thienyl or furyl;

$R^3$ is hydrogen or $R^{3P}$ where $R^5$, $R^6$ and $R^7$ are each independently unsubstituted lower alkyl (especially, methyl or ethyl);

$R^4$ is hydrogen or unsubstituted lower alkyl (especially, methyl or ethyl);

$R^5$, $R^6$ and $R^7$ are each independently unsubstituted lower alkyl (especially, methyl or ethyl);

$R^8$ is unsubstituted lower alkyl (especially methyl or ethyl); and

T is the moiety:

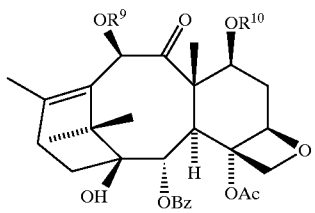

where $R^9$ is hydrogen, alkylcarbonyl, or a hydroxyl protecting group, especially acetyl; and $R^{10}$ is hydrogen or a hydroxyl protecting group, especially a trialkylsilyl group such as triethylsilyl or trimethylsilyl.

C-13 Acyloxy Sidechain-bearing Taxanes

The addition of a C-13 acyloxy sidechain as described herein, in and of itself, may impart an increased or more desirable pharmacological activity to the taxane product, or may form a taxane product which is more readily converted to a taxane having an increased or more desirable pharmacological activity than the starting compound. Exemplary taxanes which may be prepared by the present methods for the preparation of sidechain-bearing taxanes include those taxanes described in European Patent Publication No. 400,971, and U.S. patent application Ser. No. 07/995,443, filed Dec. 23, 1992 and Ser. No. 08/171,792, filed Dec. 22, 1993, all incorporated herein by reference. It is preferred to ultimately prepare taxotere or, most preferably, paclitaxel according to the methods of the present invention.

Pharmacologically active taxanes such as paclitaxel may be used as antitumor agents to treat patients suffering from cancers such as breast, ovarian, colon or lung cancers, melanoma and leukemia.

As can be appreciated, the oxazolidines, taxanes and other compounds described herein may be present in more than one stereoisomeric form. All stereoisomers of the compounds described herein are contemplated, whether alone (that is, substantially free of other isomers), in admixture with certain stereoisomers (for example, as a racemate) or in any other mixture thereof. It is preferred that these compounds be substantially free of other stereoisomers.

The present invention is further described by the following examples which are illustrative only, and are in no way intended to limit the scope of the present claims.

ABBREVIATIONS

The following abbreviations have the indicated meaning throughout the present specification.

Ac=acetyl
Bz=—C(O)-Ph (i.e., benzoyl)
DCC=dicyclohexylcarbodiimide
DMAP=dimethylaminopyridine
DMF=dimethylformamide
Et=ethyl
EtOAc=ethyl acetate
MOP=1-methoxy-1-methylethyl
Ph=phenyl
HI=homogeneity index
PMA=phosphomolybdic acid
PPTS=pyridinium p-toluene sulfonate
TEA=triethylamine TES=triethylsilyl
THF=tetrahydrofuran
TLC=thin layer chromatography The following Examples 1 to 4 demonstrate cyclizations forming a preferred oxazolidine ester compound of the formula I or II of the present invention.

EXAMPLE 1
Preparation of (4S-trans)-3-Benzoyl-2,2-dimethyl-4-phenyl-5-oxazolidinecarboxylic Acid, Ethyl Ester

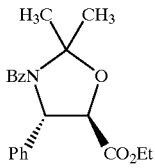

[R-(R*, S*)]-β-(Benzoylamino)-α-hydroxybenzenepropanoic acid, ethyl ester:

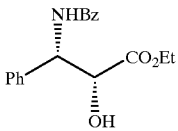

(225 mg, 0.7183 mmol) was suspended in methylene chloride (CH₂Cl₂, 3.0 ml), and DMF (2.0 ml) was added until a clear solution resulted. The mixture was cooled to 0° C., and 2-methoxypropene (1.7957 mmol) was added, followed by PPTS (approximately 5 mg, 0.016 mmol). The mixture was stirred for 4 hours, then another 2.6 eq. (1.7957 mmol) of 2-methoxypropene were added. The addition was repeated twice more at intervals of 2 hours, and the mixture was allowed to stand overnight at room temperature. The reaction was quenched with saturated NaHCO₃, and the mixture was washed with saturated NaHCO₃, dried, and the solvent removed to give the product in quantitative yield. The residue was refluxed in ar excess of toluene and 2,2-dimethoxypropane and azeotroped overnight. HPLC isolation gave 73 mg of the title product (29%).

TLC (hexanes/ethyl acetate=2:1) Rf=0.48
m.p.=87–88° C.
¹H NMR in accordance with the above structure.

EXAMPLE 2
Alternative Preparations (A) and (B) of (4S-trans)-3-Benzoyl-2,2-dimethyl-4-phenyl-5-oxazolidinecarboxylic Acid, Ethyl Ester (A) [R-(R*,S*)]-β-(Benzoylamino)-α-hydroxybenzenepropanoic acid, ethyl ester (2.200 mg) was suspended in toluene (250 ml) and the flask equipped with a Dean-Stark trap. After heating to reflux, the compound dissolved. 40 ml of toluene were distilled off, PPTS (120 mg) and 2-methoxypropene (3.5 ml) were added, and distillation was continued. Further additions of 2-methoxypropene (2 ml, and then 1 ml) and toluene (50 ml, and then another 50 ml) were made, and the distillate periodically discarded. Purification on HPLC (hexane/ethyl acetate, 3:1) gave 2.3 g (93%) of the title product in a mixture with other reaction products. (Product characteristics consistent with structure of Example 1.)

(B) [R-(R*,S*)]-β-(Benzoylamino)-α-(1-methoxy-1-methylethoxy)benzenepropanoic acid, ethyl ester:

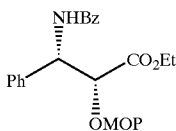

(2.200 mg) was mixed with toluene (200 ml) and PPTS (75 mg) was added. The mixture was heated and toluene removed in a Dean-Stark trap. After 70 ml of toluene were removed, a TLC was conducted which showed a mixture of products and the hydroxyester starting material of Example 1. 2-Methoxypropene (0.5 ml) was added and the distillation continued. A second charge of 2-methoxypropene (0.5 ml) was added and the distillation continued. When the volume dropped to about 70 ml, TLC showed only the title product. It was purified by HPLC (hexanes/ethyl acetate, 5:1 to 1:1) to give 1.56 mg of the title product (75% overall yield from the starting compound) in admixture with other reaction products. (Product characteristics consistent with structure of Example 1.)

EXAMPLE 3
Preparation of (4S,5S)-3-Benzoyl-2-ethoxy-4-phenyl-5-oxazolidinecarboxylic Acid Ethyl Ester

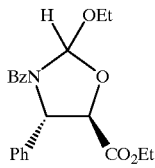

[R-(R*,S*)]-β-(Benzoylamino)-α-hydroxybenzenepropanoic acid, ethyl ester (1.16 mmol) is suspended in benzene (10 ml), and triethoxymethane (3.44 mmol) and PPTS (72 mg) are added. Heating to reflux provides the title compound.

EXAMPLE 4
Preparation of (4S,5R)-3-Benzoyl-2-methoxy-4-phenyl-5-oxazolidinecarboxylic Acid, Ethyl Ester

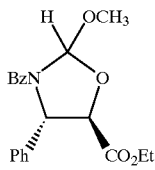

(A) [R-(R*,S*)]-β-(Benzoylamino)-α-hydroxybenzenepropanoic acid, ethyl ester (1.16 mmol) was suspended in benzene (10 ml), and trimethoxymethane (3.44 mmol) and PPTS (72 mg) were added. Heating to reflux (103° C.) did not dissolve the starting compound. 2 ml of DMF were then added so that most of the starting compound dissolved, although the solution remained somewhat turbid. The flask was equipped with a Soxhlet extractor. The thimble of the extractor was filled with 4 Å mol. sieves. After 1 hour, and approximately 3 to 4 cycles in the Soxhlet extractor, TLC showed consumption of the starting material, and a new major spot of the title product. It was diluted with EtOAc, washed with NaHCO₃ and H₂O, dried and the solvent removed. NMR showed the presence of the title product and a small impurity. The product was purified on HPLC (hexane:ethyl acetate, 3:1) to give 358 mg (87%) of the title product.

(B) Preparation of the title compound was conducted on a larger scale as follows. [R-(R*,S*)]-β-(Benzoylamino)-α-hydroxybenzenepropanoic acid, ethyl ester (3.138 g) was suspended in benzene (100 ml), and trimethoxymethane (3.190 g) and PPTS (628 mg) were added. The reaction solution was heated to reflux, 20 ml of DMF were added for dissolution of most of the starting compound, followed by heating with a Soxhlet extractor. The thimble in the extractor was filled with 4 Å mol. sieves. After 1 hour, and approximately 3 to 4 cycles in the Soxhlet extractor, TLC showed consumption of the starting material, and a new major spot of the title product. It was diluted with EtOAc, washed with $NaHCO_3$ and $H_2O$, dried and the solvent removed. NMR showed the presence of the title product and a small impurity. The product was purified on HPLC (hexane:ethyl acetate, 3:1) to give 3.138 g (97%) of the title product. The product (an oil) was a mixture of diastereomers (not separated). Mass spec.: $M+H^+=356$ TLC (hexanes/ethyl acetate=2:1) Rf=0.41

$^1H$ NMR in accordance with the above structure.

The following Examples 5 to 7 demonstrate hydrolysis of the ester group of a preferred oxazolidine ester of the formula I or II to form the corresponding carboxylic acid, or salt thereof, of the formula III or VII.

EXAMPLE 5
Preparation of (4S-trans)-3-Benzoyl-2,2-dimethyl-4-phenyl-5-oxazolidinecarboxylic Acid, Lithium Salt

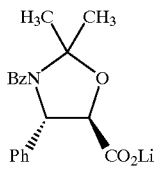

(4S-trans)-3-Benzoyl-2,2-dimethyl-4-phenyl-5-oxazolidinecarboxylic acid, ethyl ester (73 mg) was dissolved in THF (0.5 ml) at room temperature and LiOH (0.217 ml, 1M in $H_2O$) was added dropwise. Initially, a bi-phasic mixture was observed, but after the addition of the last quantity of LiOH and stirring for 5 minutes the solution became homogeneous. After further stirring for ½ hour, the solvents were removed in vacuo. The residue was azeotroped with toluene/methanol and dried at 55° C. overnight under high vacuum. The title lithium salt was obtained (no further purification).

EXAMPLE 6
Preparation of (4S-trans)-3-Benzoyl-2,2-dimethyl-4-phenyl-5-oxazolidinecarboxylic Acid

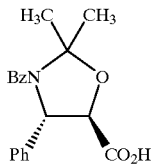

(4S-trans)-3-Benzoyl-2,2-dimethyl-4-phenyl-5-oxazolidinecarboxylic acid, ethyl ester (1.56 g) was dissolved in THF (10 ml) at room temperature and LiOH (4.63 ml, 1M in $H_2O$) was added dropwise. Initially, a bi-phasic mixture was observed, but after the addition of the last quantity of LiOH and stirring for 5 minutes the solution became homogeneous. After further stirring for ½ hour, the reaction mixture was quenched with aqueous 1N HCl (4.63 ml), and diluted with EtOAc and saturated NaCl. The $H_2O$ layer (pH=3) was twice extracted with EtOAc, and the combined organic phase dried with $MgSO_4$. The solvent was removed in vacuo to give 1.39 g of the title product acid (97%) which was homogeneous by TLC and $^1H$ NMR.

TLC (ethyl acetate/acetone/methanol/water=7:1:1:1) Rf=0.40 m.p.=173–176° C.

$^1H$ NMR in accordance with the above structure.

EXAMPLE 7
Preparation of (4S,5β)-3-Benzoyl-2-methoxy-4-phenyl-5-oxazolidinecarboxylic Acid

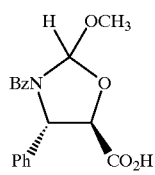

A procedure analogous to that of Example 6 was employed, substituting the title product of Example 4 (177 mg) in place of the title product of Example 1 and employing the following amounts of the remaining reagents: 0.524 ml 1N LiOH, 2.0 ml THF and 0.524 1N HCl. 161 mg of the crude title product (99%) was obtained. The same procedure was carried out at a larger scale (using 3,580 mg of the title product of Example 4, 10.38 ml of 1N LiOH, 40 ml of THF, and 10.38 ml of 1N HCl) to yield 3.23 g of the crude title product (98%) (minor impurity present). The product was a mixture of diastereomers (not separated).

TLC (ethyl acetate/acetone/methanol/water=7:1:1:1) Rf=0.35 m.p. (mixture)=160–162° C.

$^1H$ NMR in accordance with the above structure.

The following Example 8 demonstrates the preparation of a preferred starting C-13 hydroxyl-bearing taxane material of the formula IV.

EXAMPLE 8
Preparation of 7-Triethylsilylbaccatin III

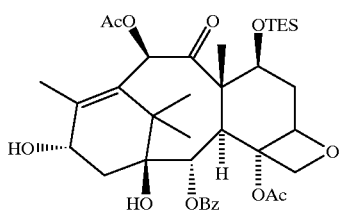

(i) [2aR-(2aα,4β,9α,11β,12α,12aα,12bα)]Benzoic Acid, 12b-acetyloxy-2a,3,4,4a,5,6,9,10,11,12,12a,12b-dodecahydro-6,9,11-trihydroxy-4a,8,13,13-tetramethyl-5-oxo-4-[(triethylsilyl)oxy]-7,11-methano-1H-cyclodeca[3,4]benz[1,2-b]oxet-12-yl Ester (7-O-TES-10-Desacetylbaccatin III)

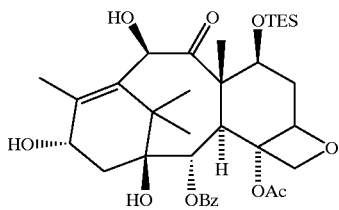

10-Desacetylbaccatin III (27.4 g, 50.3 mmol) (amount not corrected for impurities measured (twice) as: $H_2O$: 1.0% (1.57%), $CH_3OH$: 1.49% (1.6%), ethyl acetate: 0.1% (0.09%), hexane (0.03%)) and 4-dimethylaminopyridine (2.62 g, 21.4 mmol) (wt. % $H_2O$ (K.F.)=0.09) were added to a flame-dried, argon purged 1 L 3-necked flask (equipped with a mechanical stirrer and a digital thermometer) and were dissolved in dry dimethylformamide (122 ml) (wt. % $H_2O$ (K.F.)=<0.01). $CH_2Cl_2$ (256 ml) (wt. % $H_2O$ (K.F.)=<0.01) was added and the resulting homogeneous solution was cooled to −50° C. (The temperature of the reaction solution rose from 23° C. to 25° C. during the addition of $CH_2Cl_2$.) Triethylamine ($NEt_3$, 16 ml, 120 mmol) (wt. % $H_2O$ (K.F.)=0.08) was added dropwise over 3 minutes and the resulting solution was stirred at −50° C. for 5 minutes before the dropwise addition of neat triethylsilyl chloride ($Et_3SiCl$, 18.6 ml, 111 mmol). The addition of $Et_3SiCl$ was conducted over a period of 10 minutes and the temperature of the reaction did not rise above −50° C. The reaction became very cloudy during the addition of $Et_3SiCl$. The resulting mixture was stirred at ∼−50° C. for 1 hour and was then allowed to stand (without stirring) in a −48° C. freezer for 22 hours. (A separate experiment showed that stirring the reaction at −48° C. for 8 hours resulted in ∼60% conversion.) The mixture was then removed from the freezer and warmed to ∼−10° C. (TLC analysis of the mixture (solvent: ethyl acetate, stain: phosphomolybdic acid/ethanol) revealed the absence of starting material and showed a single spot for the product (Rf=0.60).) The cold mixture was combined with EtOAc (1L) and washed with $H_2O$ (890 ml). The resulting aqueous layer was separated and extracted with EtOAc (250 ml). The combined organic layers were washed with 5.7% aqueous $NaH_2PO_4$ (2×250 ml) (measured pH of 5.7% aqueous $NaH_2PO_4$=4.30±0.05; measured pH of the combined $NaH_2PH_4$ washings=5.75±0.05), half-saturated aqueous NaCl (250 ml), saturated aqueous NaCl (250 ml), dried over $Na_2SO_4$, filtered and concentrated on a rotovap. (All concentrations on the rotovap were conducted with a water bath temperature of 35° C.) The resulting semi-solid was further dried by exposure to high vacuum (∼1 mm Hg for 20 minutes) to give 41.5 g of a white solid. The crude product was then dissolved in $CH_2Cl_2$ (400 ml) (heating in a 35° C. water bath was required to dissolve the solid) and the volume of the resulting solution was reduced to ∼150 ml on a rotovap. Crystallization started immediately and the mixture was allowed to stand at room temperature for 1 hour. Hexanes (100 ml) were added and the mixture was gently swirled. The mixture was allowed to stand in a 4° C. cold room for 16.5 hours. The solid was filtered, washed with 1:9 $CH_2Cl_2$/hexanes (3×250 ml) on a suction filter, and dried under high vacuum (∼0.2 mm Hg for 42 hours) to give 26.1 g (79%) of the title product as a white powder. The mother liquor was concentrated on a rotovap and the residue was crystallized from $CH_2Cl_2$ to give 4.5 g (14%) of the title product as white crystals. Recrystallization was conducted in the same manner as with the first crop of product: the solid was dissolved in $CH_2Cl_2$ (100 ml) without heating and the volume of the resulting solution was reduced to ∼7 ml on a rotovap. Crystallization began within 5 minutes. The mixture was allowed to stand at room temperature for 1 hour, then in a 4° C. cold room for 42 hours. The crystals were filtered, washed with 1:9 $CH_2Cl_2$/hexanes (3×50 ml) on a suction filter, and dried under high vacuum (∼0.2 mm Hg for 18 hours.). The $^1H$ NMR of this crop was identical to the $^1H$ NMR of the first crop of product.

The combined yield for the two crops was 93% (uncorrected).

Elemental Analysis (%)

$C_{35}H_{50}O_{10}Si$

|   | Calcd. | Found |
|---|---|---|
| C | 63.80 | 63.43 |
| H | 7.65 | 7.66 |
| $KF(H_2O)$ | 0.00 | 0.00 | mp: 239–242° C. (decomp.)

$[\alpha]^{22}_D$: −53.6° (c 1.0, $CHCl_3$)

TLC: $R_f$=0.60 (silica gel, EtOAc); visualized by phosphomolybdic acid/ethanol.

An alternative procedure was employed as follows:

In a flame-dried 250 ml 3-necked flask equipped with an argon inlet was placed 10-des-acetylbaccatin III (5.44 g, 10 mmol, having a water content of 1.56 wt. % and a methanol content of 1.6 wt %), 4-dimethylaminopyridine (0.49 g, 4 mmol) and N,N-dimethylformamide (24 ml, dried over 4 Å molecular sieve). The mixture was stirred at room temperature until homogeneous. Dichloromethane (50 ml, HPLC grade, used without purification) was added and the temperature was lowered to −50° C. Triethylamine (2.9 ml, 21 mmol) was added dropwise over a 5 minute period, followed by triethylsilylchloride (3.4 ml, 20 mmol) over a 10 minute period. The mixture was allowed to stand at −48° C. for a period of 21 hours, diluted with 200 ml of ethyl acetate and 175 ml of water. (The reaction was monitored by TLC using EtOAc as eluent: $R_f$ for the starting material=0.56, $R_f$ for the product=0.83; UV and PMA visualization.) The aqueous layer was separated and extracted with ethyl acetate (50 ml×1). The organic layers were combined and washed with 5% aqueous potassium phosphate mono basic (50 ml×2) (pH of 5% $KH_2PO_4$ in $H_2O$ was 4.3), half-saturated sodium chloride (50 ml×1), brine (50 ml×1), dried over sodium sulfate and concentrated in vacuo to give crude title product as a solid (7.45 g). The crude material was dissolved in 75 ml of hot dichloromethane and the total volume was reduced to 30 ml by heating to begin crystallization. It was set aside at room temperature for 2 hours and 4° C. for 16 hours. The crystals were filtered on a buchner funnel, washed with cold 10% dichloromethane in hexane (25 ml) and dried in vacuo to afford 5.38 g of title product. The mother liquors and washings were concentrated in vacuo and the solid residue was crystallized by dissolving in 8 ml of dichloromethane. Following the above crystallization procedure, 0.72 g of the product was obtained as a second crop. The combined yield of the title product 7-TES-10-desacetylbaccatin III, as a white solid (m.p. 238–240° C.), was 6.10 g (93%).

Elemental Analysis (%)
$C_{35}H_{50}O_{10}Si$

|   | Calcd. | Found |
|---|--------|-------|
| C | 63.80  | 63.76 |
| H | 7.65   | 7.66  | mp: 239–242° C.
$[\alpha]_D$: −53.7 (c 1.0, $CHCl_3$)
TLC: $R_f$=0.53 (silica gel, 50% EtOAc in hexane); UV and PMA visualization. HI=98.9%
(ii) [2aR-(2aα,4β,4aβ,6β,9α,11β,12α,12aα,12bα)]-6,12b-Bis(acetyloxy)-12-(benzoyloxy)-2a,3,4,4a,5,6,9,10,11,12,12a,12b-dodecahydro-9,11-dihydroxy-4a,8,13,13-tetramethyl-4-[(triethylsilyl)oxyl-7,11-methano-1H-cyclodeca[3,4]benz[1,2-b]oxet-5-one (7-O-TES-baccatin III)

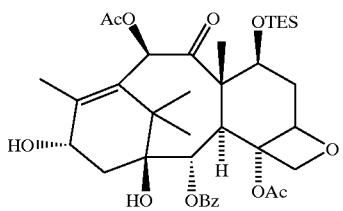

7-O-TES-10-desacetylbaccatin III prepared in step (i) above (21.4 g, 32.4 mmol) was added to a flame-dried, argon purged 1 L 3-necked flask (equipped with a mechanical stirrer and a digital thermometer) and dissolved in THF (350 ml, freshly distilled from sodium/benzophenone). The resulting solution was cooled to −70° C. A solution of n-butyllithium (n-BuLi, 14.6 ml of a 2.56 M solution in hexanes, 37.3 mmol, titrated in triplicate with diphenylacetic acid in THF at 0° C.) was added dropwise over a period of 23 minutes. The temperature of the reaction did not rise above −68° C. during the addition. Solids were formed upon the addition of n-BuLi and did not appear to dissolve at −70° C. The resulting mixture was stirred at −70° C. for 20 minutes and was then warmed to −48° C. (A clear homogeneous solution was obtained upon warming to −48° C.) After stirring at −48° C. for ½ hour, acetic anhydride (4.6 ml, 49 mmol, distilled (137–138° C., 1 atm) under an atmosphere of argon before use) was added dropwise over 7 minutes. The temperature of the reaction did not rise above −45° C. during the addition. The resulting solution was stirred at −48° C. for 20 minutes and then at 0° C. for 1 hour. The solution was diluted with ethyl acetate (350 ml), washed with saturated aqueous $NH_4Cl$ (250 ml), and the layers were separated. The aqueous layer was extracted with ethyl acetate (200 ml). The combined organic layers were washed with saturated aqueous NaCl, dried over $Na_2SO_4$, filtered, and concentrated on a rotovap. (All concentrations on the rotovap were conducted with a water bath temperature of 35° C.) Exposure of the semi-solid to high vacuum (~1.5 mm Hg for ½ hour) gave 24.7 g of a white solid. The crude product was dissolved in $CH_2Cl_2$ (300 ml) and the volume of the resulting solution was reduced to ~70 ml on a rotovap. Crystallization began within one minute. The mixture was allowed to stand at room temperature for 45 minutes, and then in a 4° C. cold room for 18 hours. The crystals were filtered, washed with 1:9 $CH_2Cl_2$/hexanes (3×100 ml) on a suction filter, and dried under high vacuum (~0.2 mm Hg for 19 hours) to give 20.9 g (92.0%) of the title product as fine white needles. The mother liquor was concentrated on a rotovap and the residue was crystallized from $CH_2Cl_2$/hexanes to give 0.82 g (3.6%) of the title product as small white crystals. Crystallization was conducted as follows: The residue was dissolved in, $CH_2Cl_2$ (10 ml) and the volume of the resulting solution was reduced to ~5 ml on the rotovap. After standing at room temperature for ½ hour, no crystals had formed. Hexanes (5 ml) were added in 1 ml portions and the solution was swirled. A few crystals were present by this time. The mixture was allowed to stand at room temperature for ½ hour (more crystals formed) and then in a 4° C. cold room for 18 hours. The crystals were filtered, washed with 1:9 $CH_2Cl_2$/hexanes on a suction filter, and dried under high vacuum (~0.15 mm Hg for 21 hours).

The combined yield for the two crops was 95.6%.
mp: 218–219° C. (decomp.)
$[\alpha]^{22}_D$: −78.4° (c 1.0, $CHCl_3$)
TLC: $R_f$=0.37 (silica gel, 1:9 acetone/$CH_2Cl_2$); visualized by phosphomolybdic acid/ethanol.

The following Examples 9 to 11 demonstrate the coupling of a preferred oxazolidine carboxylic acid of the formula III or VII with a C-13 hydroxyl-bearing taxane of the formula IV.

EXAMPLE 9

Preparation of [2aR-(2aα,4β,4aβ,6β,9α(4S*,5R*),11α,12α,12aα,12bα]]-3-Benzoyl-2,2-dimethyl-4-phenyl-5-oxazolidinecarboxylic Acid 6,12b-bis(acetyloxy)-12-(benzoyloxy)-2a,3,4,4a,5,6,9,10,11,12,12a,12b-dodecahydro-11-hydroxy-4a,8,13,13-tetramethyl-5-oxo-4-[(triethylsilyl)oxyl-7,11-methano-1H-cyclodeca[3,4]benz[1,2-b]oxet-9-yl Ester

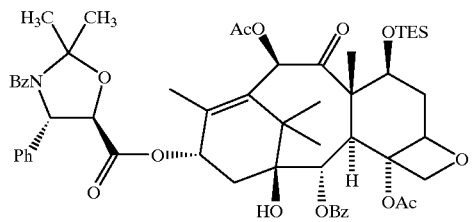

7-Triethylsilylbaccatin III (156 mg), the title product of Example 6 (94 mg), toluene (0.6 ml), DCC (69 mg) and DMAP (27 mg) were mixed together and the resulting mixture was heated at 80° C. for 3 hours. TLC at that time showed complete consumption of the 7-triethylsilylbaccatin III starting material and the appearance of a new spot. The reaction mixture was diluted with $CH_2Cl_2$ (20 ml), saturated aqueous $NaHCO_3$ (10 ml) was added, the $H_2O$ layer was extracted with $CH_2Cl_2$ (2×10 ml) and the combined organic layers were dried over anhydrous $MgSO_4$. Upon concentration in vacuo some precipitate was formed which was removed by filtration. The compound was purified by preparative HPLC (hexane:ethyl acetate, 2:1) to give 214 mg (96%) of the title product.

Mass spec.: $M+H^+$=1,008
TLC (hexanes/ethyl acetate=1:1) Rf=0.56
m.p.=164–165° C.
$^1H$ NMR in accordance with the above structure.

The above procedure was repeated on a larger scale employing 7-triethylsilylbaccatin III (475 mg), the title product of Example 6 (287 mg), toluene (1.8 ml), DCC (210 mg) and DMAP (50 mg). HPLC chromatography yielded 666 mg (98%) of the title product.

EXAMPLE 10

Alternative Preparation of [2aR-(2aα,4β,4aβ,6β,9α(4S*,5R*),11α,12α,12aα,12bα]]-3-Benzoyl-2,2-dimethyl-4- phenyl-5-oxazolidinecarboxylic Acid 6,12b-bis(acetyloxy)-12-(benzoyloxy)-2a,3,4,4a,5,6,9,10,11,12,12a,12b-dodecahydro-11-hydroxy-4a,8,13,13-tetramethyl-5-oxo-4-[(triethysilyl)oxy]-7,11-methano-1H-cyclodeca[3,4]benz[1,2b]oxet-9-yl Ester A suspension of the title product of Example 6 (103 mg), bis(2-oxo-3-oxazolidinyl)phosphinic chloride (65 mg) having the structure:

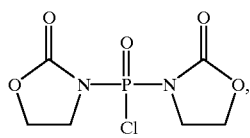

and 7-triethylsilylbaccatin III (170 mg) in CH$_2$Cl$_2$ (0.5 ml) and TEA (0.068 ml) was stirred at room temperature for 3 hours. After ½ hour the suspension became a somewhat cloudy solution. No reaction was observed by TLC. The mixture was then heated under reflux for 1 hour (no reaction). At that time, DMAP was added and heating continued for 1 hour resulting in product formation. The mixture was diluted with ethyl acetate, washed with saturated aqueous NaHCO$_3$, pH 3 phosphate buffer, saturated aqueous NaCl, dried and evaporated to give 232 mg (95%) of the crude product. $^1$H NMR showed the desired title product and about 2 to 5% starting material. (Product characteristics consistent with structure of Example 9.)

EXAMPLE 11

Preparation of [2aR-(2aα,4β,4aβ,6β,9α(4S*,5R*),11α,12α,12aα,12bα]]-3-Benzoyl-2-methoxy-4-phenyl-5-oxazolidinecarboxylic Acid 6,12b-bis(acetyloxy)-12-(benzoyloxy)-2a,3,4,4a,5,6,9,10,11,12,12a,12b-dodecahydro-11-hydroxy-4a,8,13,13-tetramethyl-5-oxo-4-[(triethylsilyl)oxy]-7,11-methano-1H-cyclodeca[3,4]benz[1,2-b]oxet-9-yl Ester

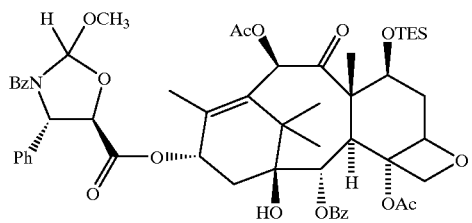

7-Triethylsilylbaccatin III (255 mg), the title product of Example 7 (155 mg), toluene (1.0 ml), DCC (113 mg) and DMAP (27, mg) were mixed together and the resulting mixture was heated to reflux (about 80° C.) for 1 hour. At that time, the reaction was not complete and a second charge of DCC (56.5 mg) and DMAP (13.5 mg) were added and the mixture was refluxed for another 2 hours. Small amounts of starting material still remained. After work-up (dilution with EtOAc, washing with saturated aqueous NaHCO$_3$, and drying with anhydrous MgSO$_4$), the product was purified on preparative HPLC. The main fractions gave 300 mg (82%) of the title product (and a small amount of impurity).

On a larger scale, 7-triethylsilylbaccatin III (1.022 g), the title product of Example 7 (620 mg), DCC (451 mg) and DMAP (107 mg) were mixed together in a dry flask and suspended in toluene (3.5 ml). The mixture was heated at 80° C. for 1 hour, then another 0.5 eq. of the title product of Example 7 was added, followed by a second charge of DMAP (107 mg) and DCC (451 mg). Starting material still remained after heating for 1 hour. The reaction mixture was heated overnight and worked-up as described above. Purification on HPLC (hexane:ethyl acetate, 9:1→1:1) gave as the first fraction 75 mg of an impurity, then the title product (928 mg, 65%). 213 mg of starting material (21%) remained. The product was a mixture of diastereomers (not separated).
TLC (hexanes/ethyl acetate=1:1) Rf=0.51
m.p. (mixture)=152–155° C.
$^1$H NMR in accordance with the above structure.

The following Examples 12 to 13 demonstrate ring opening of preferred coupled products of the formula V or VIII to yield a C-13 acyloxy sidechain-bearing taxane of the formula VI.

EXAMPLE 12
Preparation of Paclitaxel

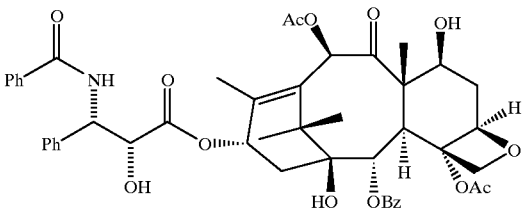

The title product of Example 11 (106 mg) was dissolved in THF (1.5 ml) and cooled to 0° C. 10% aqueous HCl (0.5 ml) and acetic acid (0.5 ml) were added. The reaction mixture was stirred at 0° C. for 5 hours. It was then stirred for 2 hours at room temperature, followed by storage overnight at 4° C. As the reaction was still not complete, the mixture was then stirred at room temperature for 5 hours after which time no starting material was detectable by TLC. After work-up (dilution with EtOAc, washing with saturated NaHCO$_3$ and brine, and drying with MgSO$_4$), it was purified by preparative HPLC (hexane:ethyl actetate, 5:1→1:2) to give 70 mg (78%) of the title product. (Product characteristics consistent with those of an authentic sample of the natural product.)

EXAMPLE 13
Preparation of Paclitaxel

The title product of Example 9 (0.084 mmol) was dissolved in acetone (1.0 ml), Pd(CH$_3$CN)$_2$Cl$_2$ (0.5 mg) was added (from tip of spatula), and the mixture was stirred at room temperature. After 2 hours, deprotection of the 7-triethylsilyl group was observed to a small extent (additional polar spots on TLC were observed). Further stirring gave additional deprotection of the 7-triethylsilyl group, although some starting material still remained. Another portion of Pd(CH$_3$CN)$_2$Cl$_2$ (0.5 mg) was added and stirring was continued overnight. At this time, paclitaxel, the starting acetonide taxane and an analog of the starting acetonide taxane in which the 7-position triethylsilyl group had been deprotected to form a hydroxyl group were observed by TLC. A third portion of Pd(CH$_3$CN)$_2$Cl$_2$ (0.5 mg) was added and stirring was continued for 8 hours (deprotecting the 7-position triethylsilyl group; at this time, a small amount of starting material remained with amounts of impurities more polar than paclitaxel). The reaction mixture was quenched with saturated NaHCO$_3$, worked up by diluting with ethyl acetate, washing with H$_2$O followed by saturated aqueous NaCl, and drying with anhydrous MgSO$_4$. The solvents were removed in vacuo and the residue was purified by HPLC (hexane:ethyl acetate, 2:1→1:2) to yield 30 mg (42%) of the title product (paclitaxel). (Product characteristics consistent with those of an authentic sample of the natural product.)

What is claimed is:

1. A compound of formula I or a salt thereof:

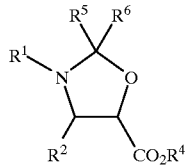

(I)

wherein
- $R^1$ is hydrogen or alkylcarbonyl;
- $R^2$ is aryl, heterocyclo, or alkyl;
- $R^4$ is hydrogen, alkyl, alkenyl, alkynyl, aryl, cycloalkyl, cycloalkenyl, or heterocyclo; and
- $R^5$ and $R^6$ are (a) each independently alkyl; or (b) together with the carbon atom to which they are bonded form a cycloalkyl, cycloalkenyl, or heterocyclo group.

2. A compound of formula V or a salt thereof:

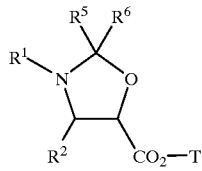

(V)

wherein
- $R^1$ is hydrogen or alkylcarbonyl;
- $R^2$ is aryl, heterocyclo, or alkyl;
- $R^5$ and $R^6$ are (a) each independently alkyl; or (b) together with the carbon atom to which they are bonded form a cycloalkyl, cycloalkenyl, or heterocyclo group; and
- T is a taxane moiety directly bonded at C-13 of said moiety.

3. A compound of formula II or a salt thereof:

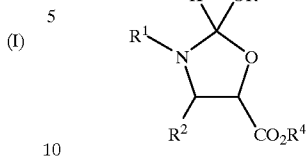

(II)

wherein
- $R^1$ is hydrogen, arylcarbonyl, alkoxycarbonyl, or alkylcarbonyl;
- $R^2$ is aryl, heterocyclo, or alkyl;
- $R^4$ is hydrogen, alkyl, alkenyl, alkynyl, aryl, cycloalkyl, cycloalkenyl, or heterocyclo; and
- $R^8$ is aryl.

4. A compound of formula VIII or a salt thereof:

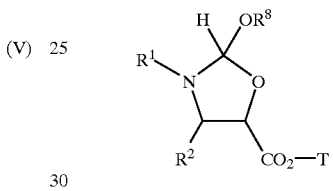

(VIII)

wherein
- $R^1$ is hydrogen, arylcarbonyl, alkoxycarbonyl, or alkylcarbonyl;
- $R^2$ is aryl, heterocyclo, or alkyl;
- $R^8$ is aryl; and
- T is a taxane moiety directly bonded at C-13 of said moiety.

* * * * *